(12) United States Patent
Mazzone et al.

(10) Patent No.: US 8,333,757 B2
(45) Date of Patent: Dec. 18, 2012

(54) BIASING A CATHETER BALLOON

(75) Inventors: James Mazzone, San Jose, CA (US); Desmond Cheung, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 609 days.

(21) Appl. No.: 12/562,386

(22) Filed: Sep. 18, 2009

(65) Prior Publication Data

US 2010/0076402 A1 Mar. 25, 2010

Related U.S. Application Data

(60) Provisional application No. 61/099,021, filed on Sep. 22, 2008.

(51) Int. Cl.
*A61B 18/02* (2006.01)
(52) U.S. Cl. ......................................................... 606/21
(58) Field of Classification Search ............... 606/20–26
See application file for complete search history.

(56) References Cited

U.S. PATENT DOCUMENTS

| | | | |
|---|---|---|---|
| 4,315,512 A | 2/1982 | Fogarty | |
| 5,209,727 A | 5/1993 | Radisch et al. | |
| 5,423,755 A | 6/1995 | Kesten et al. | |
| 6,575,933 B1 * | 6/2003 | Wittenberger et al. | 604/101.02 |
| 6,635,054 B2 * | 10/2003 | Fjield et al. | 606/27 |
| 6,733,439 B2 | 5/2004 | Zigler | |
| 6,964,661 B2 * | 11/2005 | Rioux et al. | 606/41 |
| 7,172,589 B2 | 2/2007 | Lafontaine | |
| 7,425,212 B1 * | 9/2008 | Danek et al. | 606/47 |
| 2002/0173785 A1 * | 11/2002 | Spear et al. | 606/41 |
| 2005/0177147 A1 | 8/2005 | Vancelette et al. | |

FOREIGN PATENT DOCUMENTS

| | | |
|---|---|---|
| EP | 0 724 891 | 8/1996 |
| EP | 1 120 129 | 8/2001 |
| GB | 1 288 033 | 9/1972 |
| JP | 2001-238953 | 9/2001 |
| WO | WO 02/07625 | 1/2002 |
| WO | WO 2008/000066 | 1/2008 |
| WO | WO 2009/009472 | 1/2009 |

OTHER PUBLICATIONS

Authorized officer Wolfgang Urack, International Search Report/Written Opinion in PCT/US2009/57452 mailed Nov. 25, 2009, 15 pages.

* cited by examiner

*Primary Examiner* — Michael Peffley
*Assistant Examiner* — Daniel Fowler
(74) *Attorney, Agent, or Firm* — Seager, Tufte & Wickhem, LLC

(57) ABSTRACT

A catheter can include a shaft; an inflatable balloon having a proximal end that is anchored to an end of the shaft; an elongate member that is separate from and disposed inside the shaft, extends into an interior chamber of the balloon, and is anchored to a distal end of the balloon; and a spring member that exerts a distally-oriented longitudinal force on the elongate member, relative to the shaft, where the distally-oriented longitudinal force causes the balloon to be biased in an extended position, away from the end of the shaft. The catheter can further include a sheath that surrounds the shaft and balloon before a treatment procedure. The balloon can be configured to be advanced outside the sheath during a treatment procedure and inflated, and the spring member can be configured to facilitate deflation and withdrawal of the balloon into the sheath following the procedure.

22 Claims, 9 Drawing Sheets

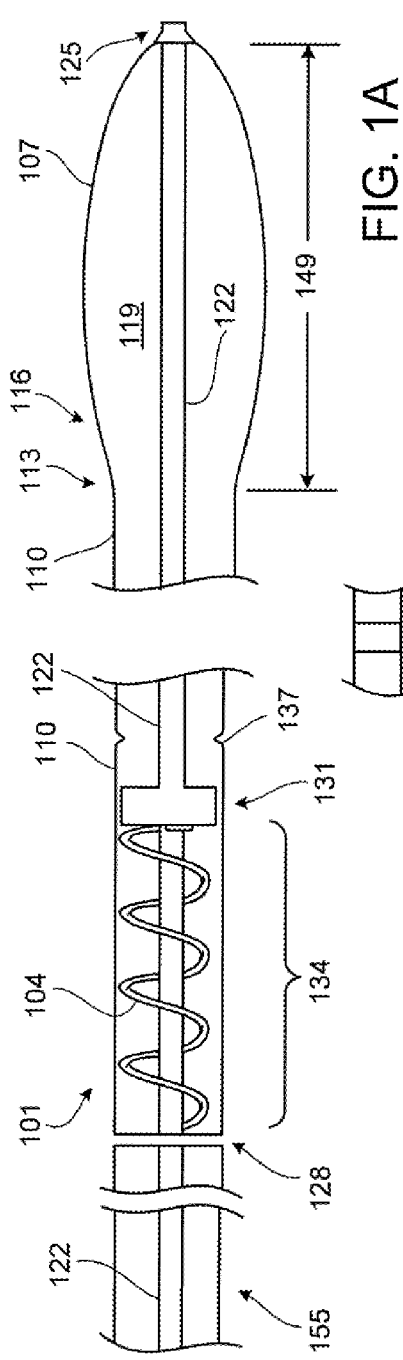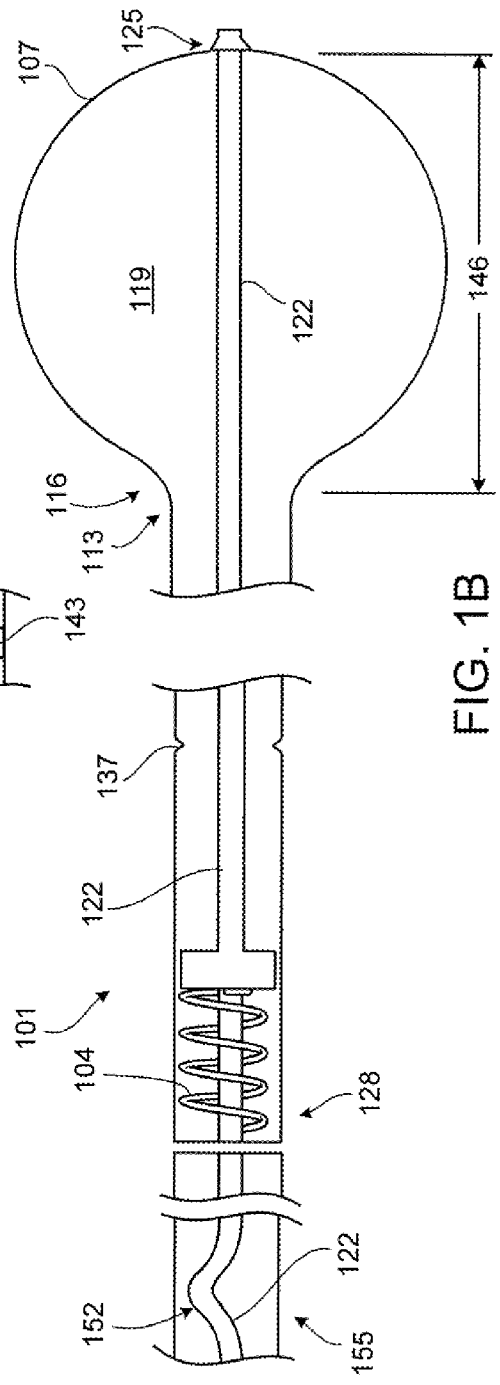

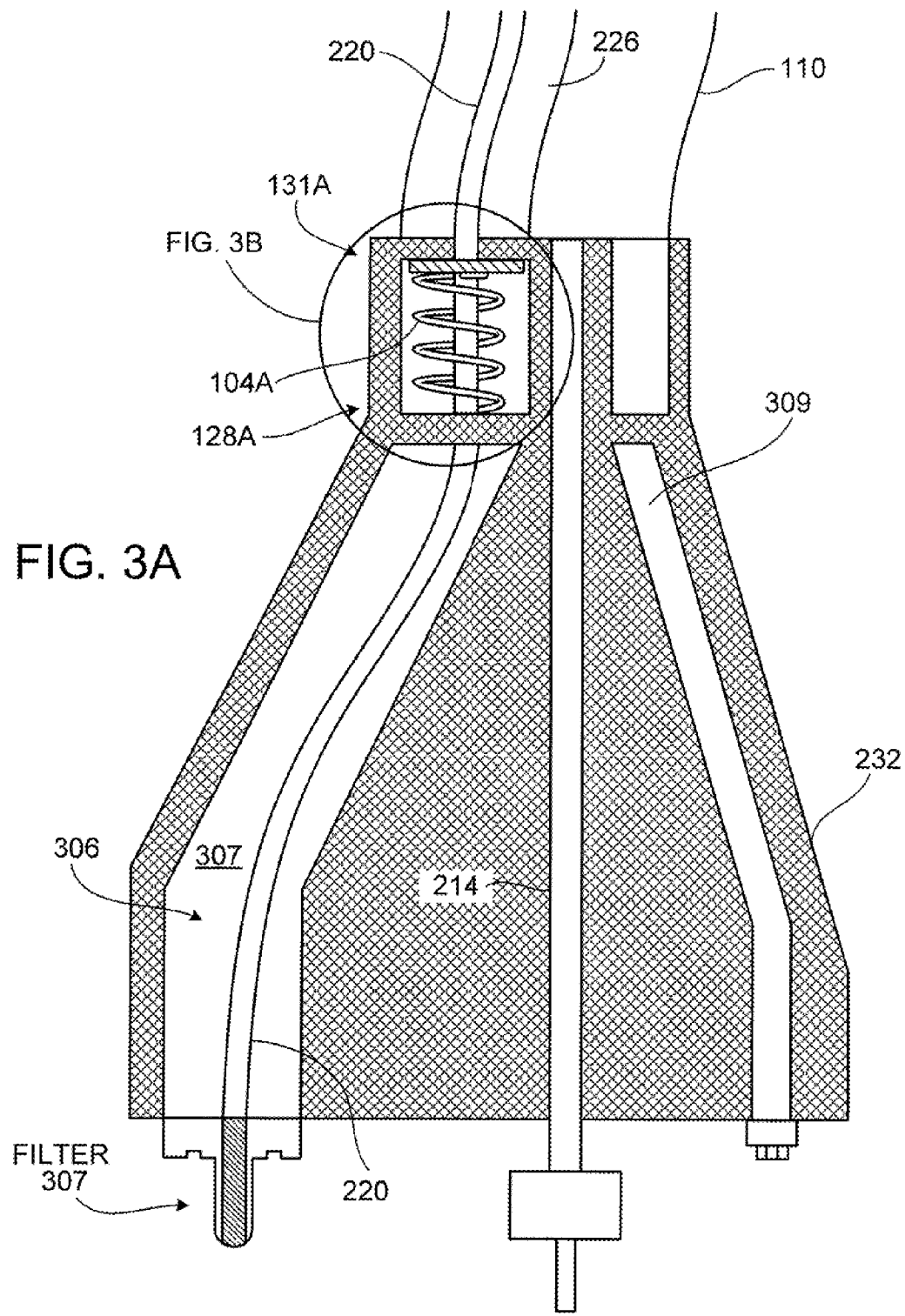

VIEW B-B

BIASING A CATHETER BALLOON

CROSS-REFERENCE TO RELATED APPLICATIONS

This application claims priority under 35 U.S.C. §119(e) to U.S. Provisional Patent Application Ser. No. 61/099,021, filed on Sep. 22, 2008, the entire contents of which are hereby incorporated by reference.

BACKGROUND

A number of medical conditions may be treated in a minimally invasive manner with various kinds of catheters designed to reach treatment sites internal to a patient's body. Balloon catheters, in particular, may be employed, for example, in angioplasty procedures, to widen obstructed blood vessels and optionally deliver stents; or in procedures to treat atrial fibrillation, such as by electrically isolating a patient's pulmonary veins. In some procedures, expansion of the balloon at the treatment site provides the desired therapy, such as expanding an obstructed blood vessel during an angioplasty procedure. In other procedures, an energy source within the balloon delivers the desired therapy, and the balloon serves to either position the energy source or communicate energy from or to tissue being treated. For example, in procedures for treating atrial fibrillation by electrically isolating pulmonary veins, a balloon catheter can be used to position a radio frequency energy source in proximity to the pulmonary vein tissue to be treated; similarly, in cryoablation procedures for treating the same condition, a cryotherapy balloon catheter can be used to extract heat, through the surface of the balloon, from the pulmonary vein tissue.

SUMMARY

During a procedure involving a balloon catheter, the balloon portion of the catheter can be introduced to a treatment site inside a patient, inflated and used in delivering therapy. After the therapy is delivered at the treatment site, the balloon can be deflated, and the catheter can be withdrawn from the patient. To help deflate the balloon and permit its withdrawal from the patient, the balloon catheter can include a spring member that biases the balloon in an extended state. In such an extended state, the balloon material may be less likely to bunch up or otherwise deflate to a diameter that is larger than its pre-inflation diameter. The spring member can be disposed in various positions within the catheter, including, for example, in a proximal end of the catheter shaft, which remains outside the patient during treatment, or in a distal end of the catheter shaft, close to the balloon. To bias the balloon in an extended state, the spring member can exert a distally-oriented force on an elongate member that extends into and is anchored to a distal end of the balloon. In some implementations, the elongate member is a guidewire lumen. In other implementations, the elongate member is another type of lumen, such as a supply or exhaust lumen for delivering liquid or gas to or withdrawing liquid or gas from a chamber internal to the balloon.

A balloon catheter can include a catheter shaft; an inflatable balloon having a proximal end that is anchored to an end of the catheter shaft; an elongate member that is separate from and disposed inside the catheter shaft, extends into an interior chamber of the inflatable balloon, and is anchored to a distal end of the inflatable balloon; and a spring member that exerts a distally-oriented longitudinal force on the elongate member, relative to the catheter shaft, wherein the distally-oriented longitudinal force causes the inflatable balloon to be biased in an extended position, away from the end of the catheter shaft.

In some implementations, the spring member is disposed inside the catheter shaft and in close proximity to the end of the catheter shaft to which the inflatable balloon is anchored. In some implementations, the spring member is disposed in a port component.

The port component can be disposed at a proximal end of the catheter shaft and can include a coupling member for fluidly coupling a lumen disposed inside the catheter shaft to a device that is external to the balloon catheter. A first end of the spring member can be mounted to the port component, and a second end of the spring member can be mounted to the elongate member. The second end can be configured to slideably translate within a channel that is in the port component and adjacent to the spring member. The spring member can be configured such that the second end translates away from the inflatable balloon when the inflatable balloon is inflated, thereby compressing the spring member beyond an initial compressed state, and translates toward the inflatable balloon to exert the distally-oriented longitudinal force when the inflatable balloon is not inflated.

The elongate member can be constructed from a material that is substantially non-compressible longitudinally, such that translation of the elongate member at the port component causes a corresponding translation of the elongate member in the interior chamber of a substantially equivalent extent. The elongate member can include at least one of a braided material or a hypotube.

In some implementations, the elongate member is a guidewire lumen. In some implementations, the elongate member includes at least one of a supply lumen for providing a liquid or gas to the interior chamber, or an exhaust lumen for exhausting a liquid or gas from the interior chamber. The lumen can include the elongate member.

In some implementations, the balloon catheter further includes a sheath that surrounds the catheter shaft and the inflatable balloon before and after a treatment procedure. The inflatable balloon can be configured to be advanced to a treatment site outside the sheath and inflated during the treatment procedure, and deflated and withdrawn back into the sheath following the treatment procedure. The spring member can be configured to exert the distally-oriented longitudinal force in a manner that facilitates deflation and withdrawal of the inflatable balloon into the sheath.

In some implementations, a balloon catheter includes a catheter shaft having a distal end to which is anchored a proximal end of an inflatable balloon; a sheath that surrounds the catheter shaft, and that is configured to surround the inflatable balloon before and after a treatment procedure; wherein the inflatable balloon is configured to be moved to a treatment site outside of the sheath and inflated during the treatment procedure; an elongate member that is separate from and disposed inside the catheter shaft, extends into an interior chamber of the inflatable balloon, and is anchored to a distal end of the inflatable balloon; and a spring member that exerts a distally-oriented longitudinal force on the elongate member, relative to the catheter shaft, wherein the distally-oriented longitudinal force causes the inflatable balloon to be biased in an extended position, away from the end of the catheter shaft, in a manner that facilitates the deflation and withdrawal of the inflatable balloon into the sheath following the treatment procedure.

The spring member can be disposed in a port component at a proximal end of the catheter shaft. The port component can be configured to fluidly couple a device that is external to the balloon catheter to the interior chamber via one or more lumens disposed in the catheter shaft. The inflatable balloon can be configured to deliver cryotherapy to a treatment site internal to a patient's vasculature.

In some implementations, a method of providing therapy to a patient includes introducing a balloon catheter to a region internal to a patient and adjacent to a treatment site; advancing the balloon outside the sheath, inflating the balloon in a manner that causes the spring member to be compressed to a greater extent than an initial compressed state, and delivering with the balloon therapy at the treatment site; deflating the balloon; and withdrawing the balloon into the sheath when a spring member has biased the deflated balloon in an extended position. The balloon catheter can include a) a catheter shaft; b) an inflatable balloon having a proximal end that is anchored to an end of the catheter shaft; c) a sheath that surrounds the catheter shaft and initially surrounds the inflatable balloon; d) an elongate member that is separate from and disposed inside the catheter shaft, extends into an interior chamber of the inflatable balloon, and is anchored to a distal end of the inflatable balloon; and e) a spring member that exerts a distally-oriented longitudinal force on the elongate member, relative to the catheter shaft, to bias the inflatable balloon in an extended position, away from the end of the catheter shaft. Delivering therapy can include at least one of delivering cryotherapy, delivery radio frequency energy with a source disposed in the interior chamber, or placing a stent.

The details of one or more implementations are set forth in the accompanying drawings and the description below. Other features, objects, and advantages will be apparent from the description and drawings, and from the claims.

BRIEF DESCRIPTION OF DRAWINGS

FIGS. 1A and 1B illustrate representative portions of an example balloon catheter having a spring member that biases the balloon in an extended state.

FIGS. 3A-3D illustrate additional details of one implementation of a spring member that can be disposed at a proximal end of the catheter shown in FIG. 2.

Like reference symbols in the various drawings indicate like elements.

DETAILED DESCRIPTION

To help deflate the balloon portion of a balloon catheter and permit its withdrawal from a patient following a procedure, the balloon catheter can include a spring member that biases the balloon in an extended state. In such an extended state, the balloon material may be less likely to bunch up or otherwise deflate to a diameter that is larger than its pre-inflation diameter. The spring member can be disposed in various positions within the catheter, including, for example, in a proximal end of the catheter shaft, which remains outside the patient during treatment, or in a distal end of the catheter shaft, close to the balloon. To bias the balloon in an extended state, the spring member can exert a distally-oriented force on an elongate member that extends into and is anchored to a distal end of the balloon. In some implementations, the elongate member is a guidewire lumen. In other implementations, the elongate member is another type of lumen, such as a supply or exhaust lumen for delivering liquid or gas to or withdrawing liquid or gas from a chamber internal to the balloon.

FIGS. 1A and 1B illustrate representative portions of an example balloon catheter 101 having a spring member 104 that biases the balloon 107 in an extended state—for example, to facilitate deflation and withdrawal of the balloon 107 from a patient following a procedure. Biasing can include exerting a force that tends to cause the balloon 107 to be extended. That is, the bias force may be overcome by other forces (e.g., such as surface tension of the balloon when it is inflated), but absent other such forces, the bias force will tend to extend the balloon, preventing it from bunching up or otherwise having a larger diameter than its pre-inflation diameter. For purposes of example, FIG. 1A illustrates representative portions of the catheter 101 when the balloon 107 is deflated, and FIG. 1B illustrates representative portions of the catheter 101 when the balloon 107 is inflated.

Figure 6:
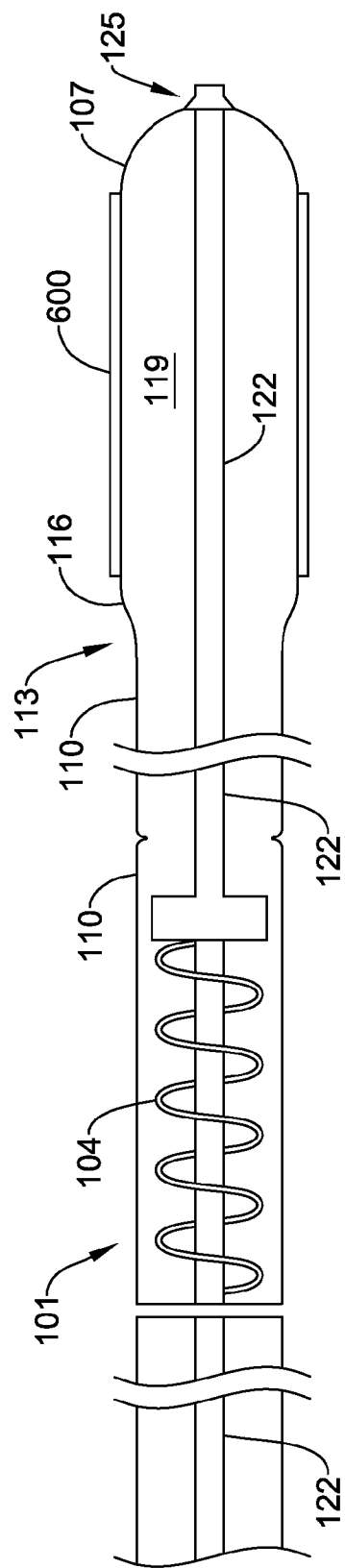
FIG. 6 illustrates an example balloon catheter with a stent disposed thereon.

The spring member 104 described herein can be included in any kind of balloon catheter that may be employed to deliver therapy to treatment sites internal to a patient. For example, the spring member 104 can be included in a cryotherapy catheter for chilling or freezing tissue internal to a patient. As another example, the spring member 104 can be included in a radio-frequency (RF) balloon catheter, such as one that may be employed to deliver RF energy to a treatment site internal to a patient. As another example, shown in FIG. 6, the spring member 104 can be included in a balloon catheter configured to deliver a medical device, such as a stent 600, to a site internal to a patient. Other types of balloon catheters may similarly benefit from the inclusion of the spring member 104.

As shown in one example, the balloon catheter 101 has a catheter shaft 110 and an inflatable balloon 107 disposed at a distal end 113 of catheter shaft 110. More specifically, a proximal end 116 of the inflatable balloon 107 is anchored to the distal end 113 of the catheter shaft 110. An interior chamber 119 can be defined by the walls or skin of the balloon 107. Although the balloon 107 is shown in FIGS. 1A and 1B as having a single wall, in some implementations, the catheter 101 can employ two separate balloons—one of which may function as a safety balloon to protect a patient from agents inside a first balloon, in the event that the first balloon ruptures or otherwise fails inside the patient. Additional details of implementations involving a safety balloons are provided below.

An elongate member 122 can be disposed inside the inflatable balloon 107. In some implementations, as depicted, the elongate member 122 is anchored to a distal end 125 of the inflatable balloon 107. In this example, the elongate member 122 is separate from and can translate within the catheter shaft 110. Another portion of the elongate member 122 is coupled to the spring member 104.

One end 128 of the spring member 104 can be anchored. In the example of FIGS. 1A and 1B, the spring member 104 is anchored to the catheter shaft 110. In other examples (e.g., those examples shown in FIG. 3A or 5), a first end 128 of the spring member 104 can be anchored to another component of the catheter 101. A second end 131 of the spring member 104 can be coupled to the elongate member 122 but can otherwise translate within a channel 134 that surrounds and is adjacent to the spring member 104. In some implementations, the channel 134 is formed by the catheter shaft 110 itself, and may be further bounded by a retaining member 137, which may keep the spring member 104 compressed to some extent, even in its most extended state, as depicted in FIG. 1A. In other implementations, the retaining member 137 does not normally contact the spring member 104 (e.g., absent a failure of the balloon 107). In some implementations, to help center the spring member 104 within the channel 134, or to couple the spring member 104 to the elongate member 122, a disc 140 or other guide can be included. Such a disc 140 is described in more detail below.

With the elongate member 122 coupled to the distal end 125 of the balloon 107 and the second end 131 of the spring member 104, the spring member 104 can apply a distally-oriented longitudinal force to the balloon 107, through the elongate member 122. So that the majority of the compression force of the spring member 104 is applied to the balloon 107, any retaining member (e.g., the retaining member 137) can be positioned such that it does not normally contact the spring member. Moreover, the elongate member 122 can be made of a substantially non-compressible material (e.g., non-compressible, minimally compressible, or rigid, particularly in the longitudinal direction). That is, the elongate member 122 can be constructed such that translation of the elongate member 122 near the spring member 104 causes a corresponding translation of the elongate member 122 inside the balloon 107 of a substantially equivalent extent (e.g., within some relatively small margin, such as, for example, within 10%, 5%, 0.5%, etc.). Suitable substantially non-compressible materials can include, for example, braided materials (e.g., plastic tubes with embedded metal braiding) or hypotubes (e.g., steel hypotubes).

To further facilitate transfer of force from the spring member 104 to the balloon 107 via the elongate member 122, the catheter shaft 110 can include one or more retaining members, such as a retaining member 143. In some implementations, the retaining member 143 allows the elongate member 122 to translate relative to the catheter shaft 110 while maintaining the elongate member 122 and catheter shaft 110 in a substantially (e.g., within a relatively small margin, such as, 25%, 10%, 5%, 0.5%, etc.) co-axial relationship.

When viewed together, FIGS. 1A and 1B illustrate the interplay between the state of the balloon 107 (e.g., whether the balloon 107 is inflated or deflated) and the state of the spring member 104 (e.g., whether and to what extent the spring member 104 is compressed). Specifically, with reference to FIG. 1B, inflation of the balloon 107 causes a distance 146 between the distal region 125 and proximal region 116 of the balloon 107 to be approximately equal to the diameter of the balloon 107—assuming a balloon that inflates to a substantially spherical shape, as shown in one example in FIG. 1B. This distance 146 is comparatively smaller than a distance 149 between the distal region 125 and proximal region 116 of the balloon 107 when the balloon is not inflated, as shown in FIG. 1A. When the balloon 107 is not inflated, as depicted in one example in FIG. 1A, the spring member 104 is in its most extended state; when the balloon 107 is inflated, as depicted in FIG. 1B, the spring member 104 can be further compressed, beyond any state of initial compression.

To accommodate the translation of the elongate member 122 on the proximal side of the spring member 104, some slack 152 can be provided in the elongate member 122. That is, for an elongate member 122 that is anchored to the catheter shaft 110 at a proximal end 155 of the catheter shaft 110, an extra length 152 of the elongate member 122 can be disposed between the proximal end 155 and the spring member 104, to accommodate for the difference between the distance 146 and the distance 149.

As will be described in more detail below, the elongate member 122 itself can serve different purposes—in addition to biasing the balloon 107. For example, in some implementations, the elongate member 122 is a guidewire lumen. In other implementations, the elongate member 122 is a supply lumen for providing a liquid or gas to the interior chamber 119. In still other implementations, the elongate member 122 can be an exhaust lumen for extracting a liquid or gas from the interior chamber 119. Additional details of the elongate member 122, and of the catheter 101 in general, are now provided with reference to FIG. 2.

Figure 2:
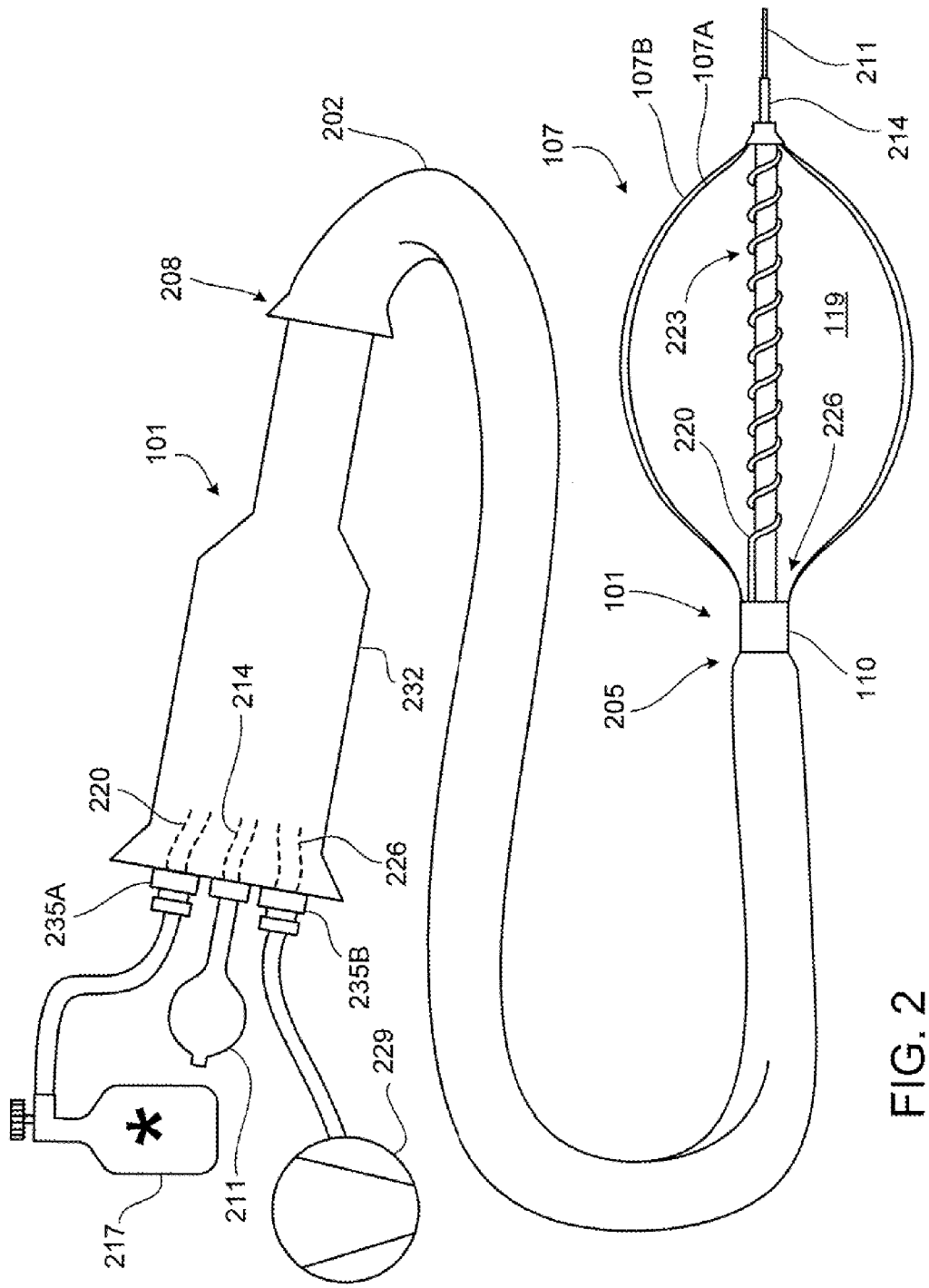
FIG. 2 illustrates additional details of the example balloon catheter shown in FIGS. 1A and 1B.

FIG. 2 illustrates additional details of the example catheter 101 shown in FIGS. 1A and 1B. As shown in the example of FIG. 2, the balloon catheter 101 is disposed in a delivery sheath 202. In other implementations, the delivery sheath 202 is not included. In some implementations that have a delivery sheath, the delivery sheath 202 is a hollow tube that can be initially placed inside a patient and subsequently used as a conduit for other medical devices, such as the balloon catheter 101. For procedures in which several catheters may be employed (e.g., catheters of different sizes or characteristics, or catheters having different functions), the delivery sheath 202 can protect the patient's internal body organs and body lumens through which the various medical devices are navigated. In addition, the delivery sheath 202 can facilitate easier navigation of other medical devices, by a physician or other technician, to a treatment site.

The delivery sheath 202 may be steerable, and it may have specific characteristics. For example, delivery sheaths may be available in varying diameters, such as 8.5 Fr (French), 10 Fr, 11 Fr, etc.; varying lengths, such as 60 cm, 65 cm, 71 cm, 78 cm, 90 cm, etc.; and having distal ends that are biased in various shapes, such as, for example, in a 15° curve, a 55° curve, a short 120° curve, a long 120° curve, etc. Different delivery sheaths may be configured for different procedures. For example, a delivery sheath having one biased curvature may be particularly effective for guiding a cryo balloon to a patient's pulmonary veins to treat atrial fibrillation, while a delivery sheath having a different biased curvature may be particularly effective for guiding a stent-delivery balloon.

In some implementations, as depicted in FIG. 2, a distal tip 205 of the delivery sheath 202 is slightly tapered to facilitate navigation of the tip 205 through a patient's vasculature, or to facilitate crossing of tissue membranes of the patient (e.g., the septal wall, during a procedure to treat atrial fibrillation). The proximal end 208 may be tapered to more easily receive other medical devices, such as the balloon catheter 101 that is shown disposed in the delivery sheath 202.

In the example of FIG. 2, the balloon catheter 101 is an over-the-wire cryotherapy balloon catheter, having a guidewire 211 disposed inside a guidewire lumen 214. The reader will appreciate that other types of balloon catheters can employ a spring member (not shown in FIG. 2) to apply a distally-oriented force to the balloon 107. For example, in other implementations, the balloon catheter 101 may not employ a guidewire 121. As another example, in other implementations, the balloon catheter 101 could be a radio frequency (RF) ablation catheter that remodels tissue with RF energy rather than by extracting heat using a cryogenic agent.

In the example cryotherapy balloon catheter 101 shown in FIG. 2, cryogenic fluid can be delivered from an external source 217 to the balloon 107 through a supply lumen 220, and released inside the interior chamber 119, through a cooling device 223 (e.g., a coiled portion of the supply lumen 220 having various orifices through which certain cryogenic agents can exit and undergo a liquid-to-gas phase change that cools the balloon 107 by the Joule-Thomson effect). Gas resulting from the cryogenic fluid being released and changing phase inside the chamber 119 can be exhausted through a separate exhaust lumen 226. In particular, for example, in some implementations, gas is exhausted through an exhaust lumen 226 to an external vacuum pump 229.

To facilitate coupling the catheter 101 to external equipment, such as the source 217 of a cryogenic agent or the vacuum pump 229, the catheter 101 can include a port component 232 having a number of coupling members 235A and 235B. The coupling members 235A and 235B can, in some implementations, terminate lumens that are internal to the catheter shaft (e.g., a supply lumen 220 and an exhaust lumen 226) with connectors (e.g., industry-standard medical connectors, proprietary medical connectors, other connectors, etc.) that facilitate connection of the lumens 220 and 226 to the external equipment (e.g., with medical tubing). As depicted in one example, the port component 232 can also provide access to the guidewire lumen 214 and corresponding guidewire 211. As shown in FIG. 2, the port component 232 is merely exemplary. Other connections and configurations are possible and contemplated (e.g., connections for pressure sensor(s), electrical sensor(s), multiple vacuum ports, etc.).

As mentioned above and shown in FIG. 2, two separate balloons 107A and 107B can be disposed on the end of the catheter shaft 110. The balloons 107A and 107B can inflate and deflate together. In some implementations, the second balloon 107B functions as a safety balloon 107B. That is, in the event that the balloon 107A ruptures or otherwise fails, the safety balloon 107B can prevent agents inside the interior chamber 119 (e.g., cryogenic agents) from directly contacting body tissue internal to the patient and can similarly prevent body tissue and body fluids from reaching the interior chamber 119. In some implementations, a separate vacuum lumen (not shown) is provided between the balloons 107A and 107B, and can be used to apply a constant vacuum force between the balloons 107A and 107B. In the event that the inner balloon 107A ruptures, the constant vacuum force can continue to evacuate any liquid and/or gas inside the interior chamber 119 and prevent the same from coming into direct contact with tissue internal to the patient. If either inner balloon 107A or outer balloon 107B ruptures, a sensor that monitors the vacuum force between the balloons 107A and 107B can detect a change and can cause an alarm to be generated or corrective action to be taken.

As mentioned above, the spring member 104 (not shown in FIG. 2) can be disposed in various positions within the catheter 101. For example, in some implementations, as described with reference to FIGS. 3A-3D, a spring member 104A is disposed in the port component 232. In other implementations, as described with reference to FIG. 4, a spring member 104B is disposed in the catheter shaft 110, in close proximity to the distal end 113 (see FIG. 1A) to which the proximal end 116 of the balloon 107 is anchored (e.g., within a short distance, such as within 10 cm, 5 cm, 1 cm, etc., or within a small percentage of the overall length of the catheter shaft, such as within 20%, 10%, 2%, etc., of the overall length). The spring member 104 can also be employed to provide distally-oriented longitudinal force to various lumens, such as, for example, a supply lumen (e.g., as described with reference to FIGS. 3A-3D and 4A-B), exhaust lumen, guidewire lumen (e.g., as described with reference to FIG. 5), or other catheter structure (e.g., another lumen, or a standalone structure).

FIG. 3A is a cutaway illustration of one example implementation in which a spring member 104A is provided in the port component 232. Specifically, as depicted in this example, the spring member 104A is coupled to the supply lumen 220 of the example cryotherapy catheter 101. More specifically, a first end 128A of the spring member 104A is anchored to the port component 232, and a second end 131A of the spring member 104A is coupled to the supply lumen 220, in order to exert a distally-oriented longitudinal force on the supply lumen 220. In this example, although the balloon 107 is not shown in FIG. 3A, the supply lumen 220 can be anchored to the distal end 125 of the balloon 107 and can otherwise translate within the catheter shaft 110.

Figure 3B:
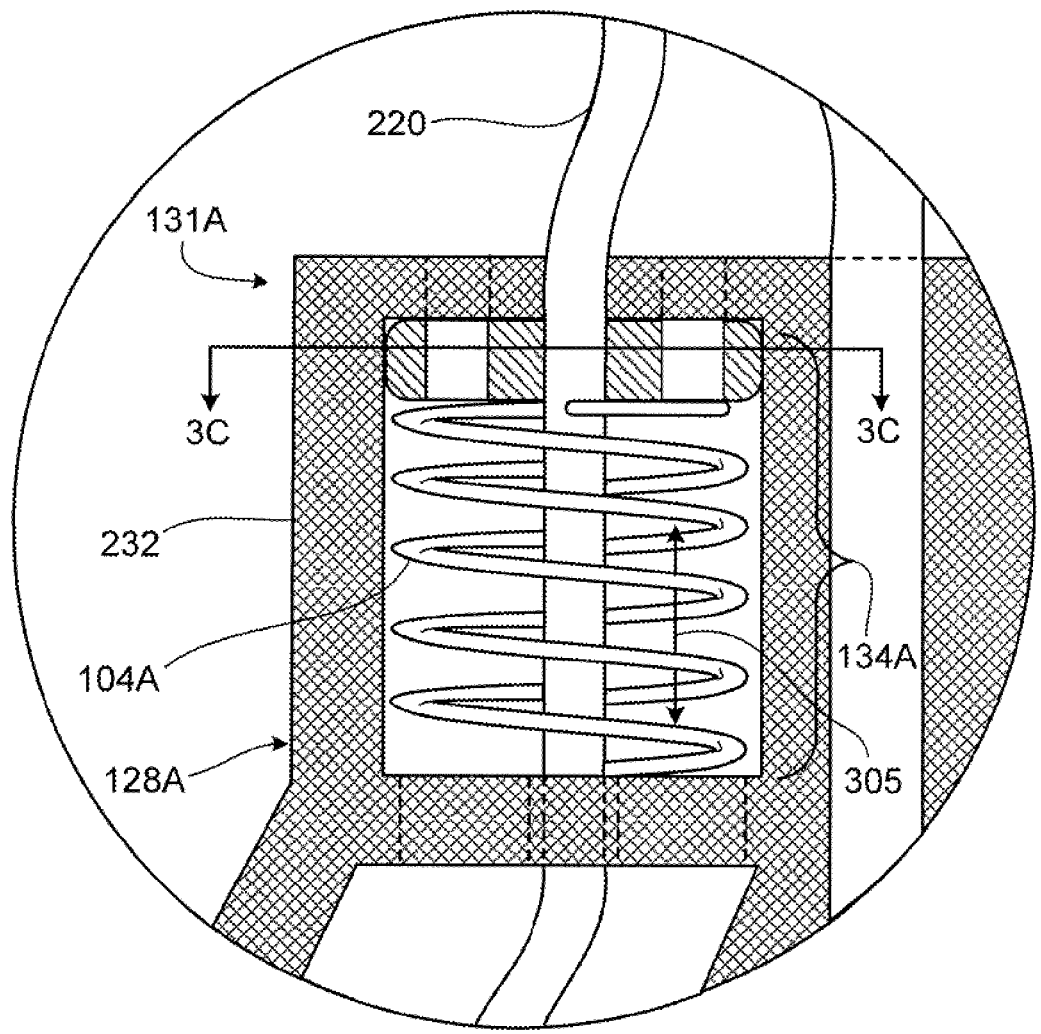

As depicted in this example, an exhaust space 303 couples to an exhaust lumen 226 in the catheter shaft 110, and within the port component 232, the exhaust space 303 is approximately coaxial with the supply lumen 220 (e.g., within some amount of deviation caused by slack 306 in the supply lumen 220). For context, a guidewire lumen 214 is shown in the port component 232, along with a secondary exhaust path 309. In some implementations, the secondary exhaust path 309 is coupled to a lumen (not shown) that evacuates the above-described space between the balloons 107A and 107B shown in FIG. 2. As shown in FIG. 3A, a filter 307 can be included in a coupling member for coupling the exhaust space 303 and/or the supply lumen 220 to the external equipment. Additional details of the spring member 104A in this implementation are now provided with reference to FIGS. 3B-3D.

FIG. 3B illustrates additional details of the spring member 104A that is shown in FIG. 3A. As depicted, the spring member 104A is anchored to the port component 232 at a first end 128A. A second end 131A is anchored to a disc 312, which can translate within a channel 134A formed in the port component 232. The disc 312 is attached to the supply lumen 220, such that as the disc 312 translates within the channel 134A (e.g., in response to the force exerted by the spring member 104A, or a force transmitted from the balloon 107 via the supply lumen 220 (e.g., when the balloon 107 is inflated). As will be described with reference to FIG. 3C, a space within the spring member 104A and around the supply lumen 220 can serve as a conduit 305 for exhaust.

Figure 3C:
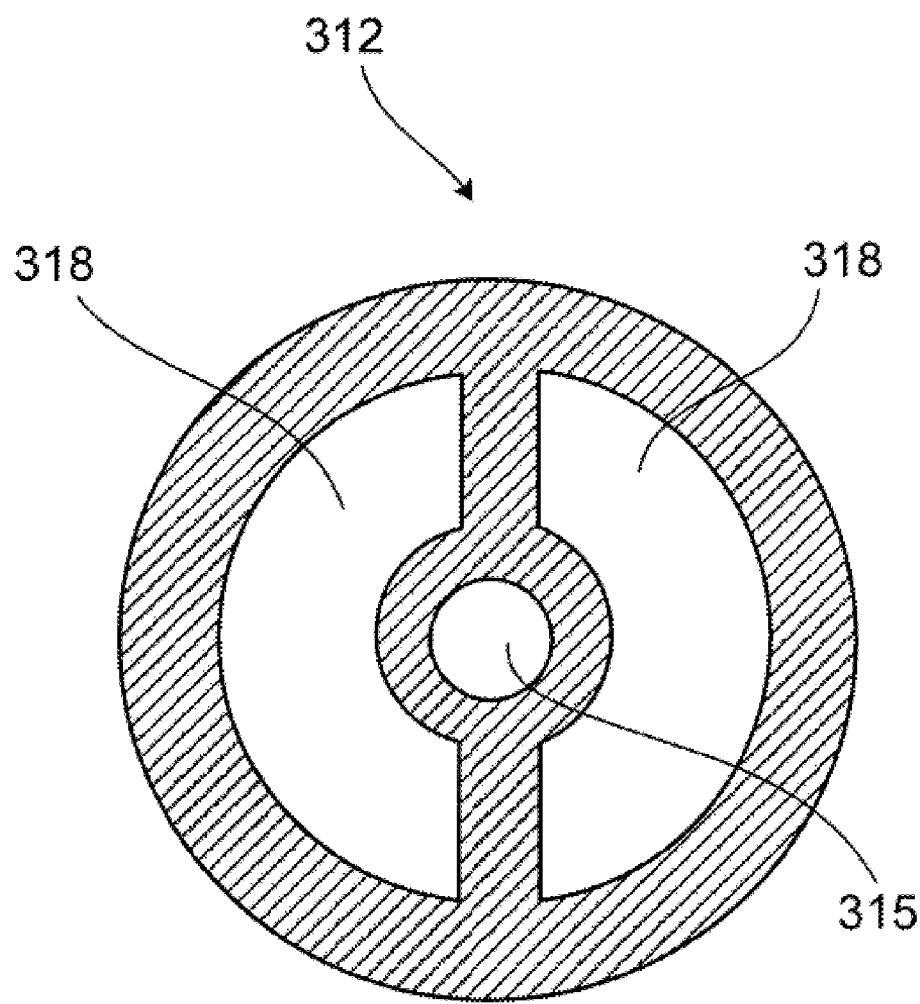
Figure 3D:
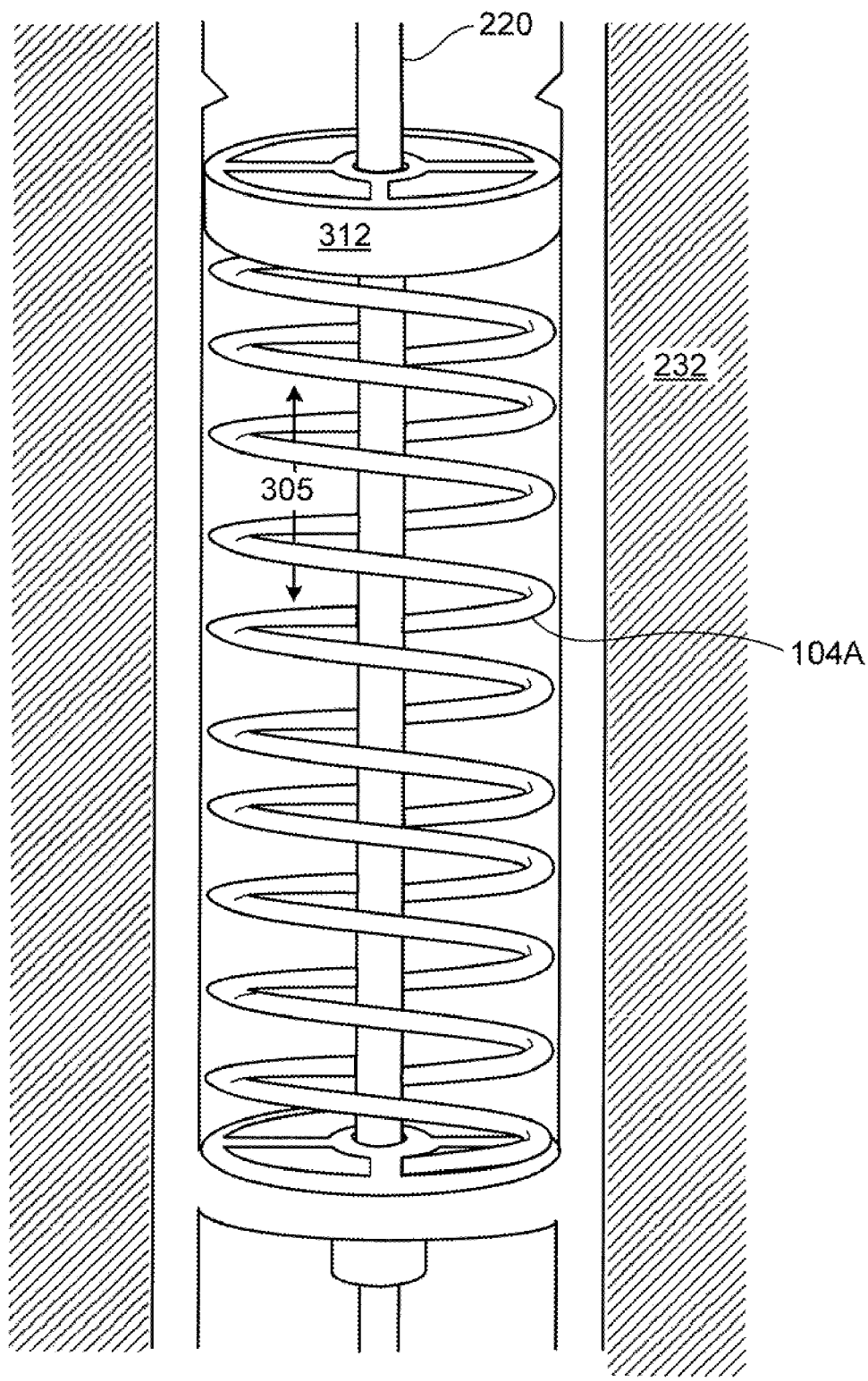

FIG. 3C illustrates additional example details of the disc 312. In the example depicted, the disc 312 is circular in shape, such that it can translate within a cylindrical channel 134A formed in the port component 232. An opening 315 is provided to receive and retain the supply lumen 220, and additional openings 318 are provided to allow exhaust to pass through the spring member 104A. FIG. 3D is a perspective view further illustrating the spring member 104A, disc 312, supply lumen 220 and exhaust conduit 305.

Figures 4A, 4B:
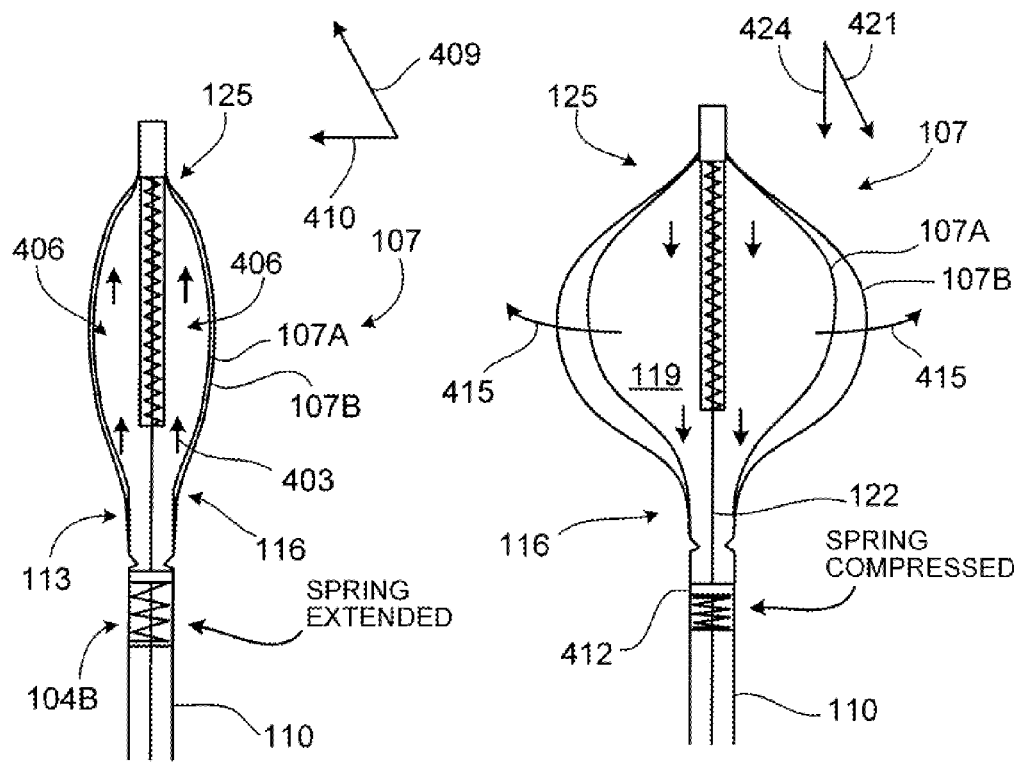
FIGS. 4A-4B illustrate additional details of another implementation of a spring member that can be disposed at a distal end of the catheter shown in FIG. 2.

FIGS. 4A and 4B illustrate another implementation in which a spring member 104B is disposed within the catheter shaft 110, in close proximity to the distal end 113 to which the proximal end 116 of the balloon 107 is anchored (e.g., within a short distance, such as within 10 cm, 5 cm, 1 cm, etc., or within a small percentage of the overall length of the catheter shaft, such as within 20%, 10%, 2%, etc., of the overall length).

FIG. 4A illustrates the balloon 107 (or more precisely, the balloons 107A and 107B, which, for simplicity, are simply referred to here as the balloon 107) in an uninflated state, with the spring extended. A distally-oriented force 403 provided by the spring member 104B biases the balloon 107 in a extended state. In particular, biasing the balloon 107 distally causes an inward force 406 to be applied to the walls of the balloon. More precisely, the force on the elongate member 122 is transferred to the walls of the balloon 107, as a tangential force 409. To the extent that the walls of the balloon are not parallel to the longitudinal force (e.g., the walls of the balloon are shown slightly bowed in FIG. 4A), the tangential force 409 has a radial component 410 that pulls the balloon walls inward.

FIG. 4B illustrates the balloon 107 in an inflated state, with the spring member 104B compressed to a greater extent than its state in FIG. 4A. In particular, pressure in the interior chamber 119, which inflates the balloon 107, applies an outward force 415 to the walls of the balloon. This outward force 415 is transferred to the walls of the balloon 107 as a tangential force 421, and as depicted, the tangential force 421 force has a longitudinal, or axial component 424, which opposes the bias force provided by the spring member 104B, causing the spring member 104B to be compressed as shown.

The spring member 104B in the example of FIGS. 4A and 4B can be coupled, for example, to a guidewire lumen (if present) or to a supply lumen. Alternatively, the spring member 104B could be coupled to a standalone balloon structure, such as a rod or other structural element specifically configured to bias the distal end 125 of the balloon in an extended state.

The spring member 104B can have a similar construction as is depicted in FIGS. 3B-3D, with appropriate modification to accommodate necessary lumens and other catheter structures that pass through or adjacent to the spring member. In particular, for example, additional openings can be disposed in a disc 412 associated with a spring member 104B, such that other lumens that are not coupled to the disc 412 can pass through the spring member 104B. Alternatively, the spring member 104B, and channel that the spring member 104B occupies, can have a smaller diameter than the catheter shaft 110 at that point, such that other lumens can pass through the catheter shaft 110 adjacent to the spring member 104B. In particular, for example, in implementations in which the spring member 104B couples to a guidewire lumen, a supply lumen can be routed adjacent to the spring member 104B, and an exhaust channel can flow through the spring member 104B as described above.

In some implementations, the spring member 104B is advantageously disposed near the distal end 113 of the catheter shaft 110. In such implementations, the spring member 104B may require less compression force to bias the balloon 107, since the compression force may not have to overcome as much resistance to the distally-oriented longitudinal force presented by the length of the elongate member 122 between the balloon 107 and the spring member 104B. In particular, a distally disposed spring member 104 may not have to overcome as much resistance presented by curves or bends in the elongate member 122 that may be present when the catheter 101 is employed to provide treatment inside a patient—particularly when the catheter 101 is routed through a tortuous vascular pathway (e.g., to reach a patient's left atrium, from the patient's right femoral artery).

Regardless of where the spring member 104 is disposed (e.g., in the distal end 113 of the catheter shaft 110, as shown in FIGS. 4A and 4B, or in the port component 232, as shown in FIG. 3A), forces and tensions of various components can be properly configured to enable the states depicted in FIGS. 4A and 4B. That is, the distally-oriented force provided by the spring member 104B should be sufficient to bias the balloon 107 in an extended state when the balloon 107 is not inflated, as shown in FIG. 4A. On the other hand, the spring member 104B should not be so stiff that it is not able to be compressed when the balloon 107 is inflated (as in FIG. 4B). Thus, for a balloon 107 whose material is very elastic, the spring member 104 may be less stiff than a spring member 104 employed with a balloon whose material is less elastic. Other forces should be considered. For example, as mentioned above, implementations in which the spring member 104A is disposed in the port component 232 (or at other, more proximal locations within the catheter shaft), the spring member 104A may need to be stiffer in order to overcome resistance to translation of the elongate member 122 that may be presented by bends or twists in the catheter shaft 110.

Figure 5:
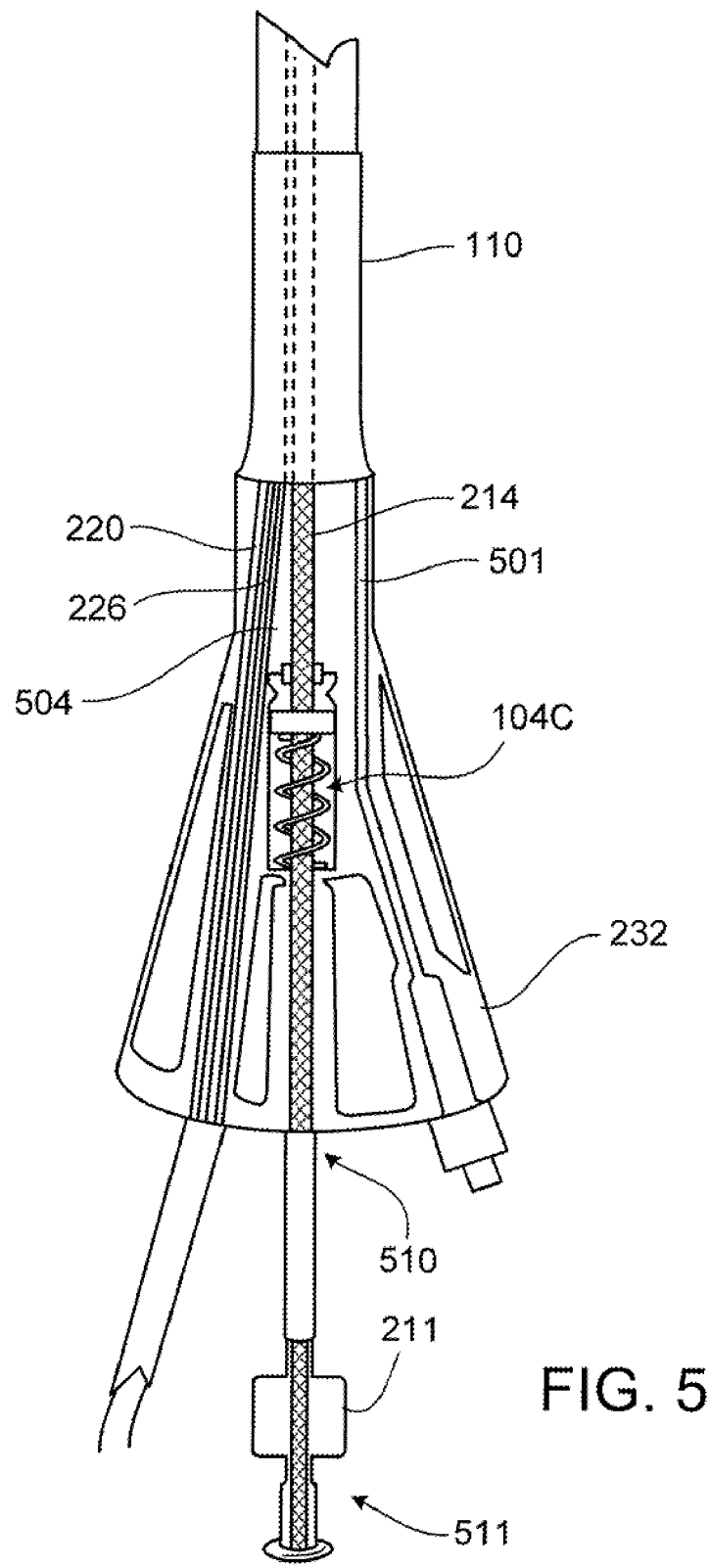
FIG. 5 illustrates additional details of another implementation of a spring member that can be disposed at the proximal end of the catheter shown in FIG. 2.

FIG. 5 illustrates another example implementation in which a spring member 104C can be disposed in the port component 232 and coupled to a central guidewire lumen. As depicted in FIG. 5, the guidewire lumen 214 can be constructed of a substantially non-compressible material, such that the majority of the distally-oriented force provided by the spring member is communicated to the distal end 125 of the balloon 107. Other lumens and structures of the catheter 101 can be disposed in any appropriate manner. As shown in one example in FIG. 5, a supply lumen 220, an exhaust lumen 226, an auxiliary exhaust lumen 501, a pressure lumen 504 (e.g., for coupling to a pressure sensor external to the catheter 101, such that pressure inside the balloon can be measured), and other lumens and structures can be routed within the catheter shaft 110 and adjacent to the guidewire lumen 214. For purposes of illustration, a proximal end 507 of the guidewire 211 itself is shown extending from the proximal end 510 of the guidewire lumen 214.

A number of implementations have been described. Nevertheless, it will be understood that various modifications may be made without departing from the spirit and scope of this document. In particular, the above description refers to a cryotherapy balloon catheter for purpose of example, but a spring member as described herein can be included in other types of balloon catheters. Cryotherapy balloon catheters are described as employing the Joule-Thomson effect to cool using a liquid-to-gas phase change, but liquid-based cryocatheters can also include spring members. The spring member can be disposed at various points within a catheter, and the specific points described herein are merely exemplary. In some implementations, the spring member can be external to the catheter; for example, the spring member could be included in a connector that couples external equipment to the catheter and could impinge on a lumen or other internal structure of the catheter to provide the distally-oriented force. Other types of port components can be employed. Multiple spring members can be employed in multiple locations. Spring members, lumens and other catheter structures can have any suitable construction, and can be made from any suitable material. In particular, for example, coiled springs are depicted by way of example, but the reader will appreciate that other devices that exert a spring force when compressed can be employed as spring members. Accordingly, other implementations are within the scope of the following claims.

What is claimed is:

1. A balloon catheter comprising:
   a catheter shaft having a proximal end and a distal end;
   an inflatable balloon having a proximal end that is anchored to the distal end of the catheter shaft;
   an elongate member that is separate from and disposed inside the catheter shaft, extends into an interior chamber of the inflatable balloon, is anchored to a distal end of the inflatable balloon, and is anchored to the proximal end of the catheter shaft; and
   a spring member that exerts a distally-oriented longitudinal force on the elongate member, relative to the catheter shaft, wherein the distally-oriented longitudinal force causes the inflatable balloon to be biased in an extended position, away from the distal end of the catheter shaft;
   wherein some slack in the form of an extra length of the elongate member is disposed between the proximal end of the catheter shaft and the spring member.

2. The balloon catheter of claim 1, wherein the spring member is disposed inside the catheter shaft and in close proximity to the distal end of the catheter shaft.

3. The balloon catheter of claim 2, wherein the elongate member comprises a guidewire lumen.

4. The balloon catheter of claim 2, wherein the elongate member comprises at least one of a supply lumen for providing a liquid or gas to the interior chamber or an exhaust lumen for exhausting a liquid or gas from the interior chamber.

5. The balloon catheter of claim 1, further comprising a port component at the proximal end of the catheter shaft, the port component having a coupling member for fluidly coupling a lumen disposed inside the catheter shaft to a device that is external to the balloon catheter.

6. The balloon catheter of claim 5, wherein the spring member is disposed in the port component.

7. The balloon catheter of claim 6, wherein a first end of the spring member is mounted to the port component, and a second end of the spring member is mounted to the elongate member; wherein the second end is configured to slideably translate within a channel that is in the port component and adjacent to the spring member.

8. The balloon catheter of claim 7, wherein the spring member is configured such that the second end translates away from the inflatable balloon when the inflatable balloon is inflated, thereby compressing the spring member beyond an initial compressed state, and translates toward the inflatable balloon to exert the distally-oriented longitudinal force when the inflatable balloon is not inflated.

9. The balloon catheter of claim 8, wherein the elongate member is disposed within the lumen.

10. The balloon catheter of claim 9, wherein the elongate member is configured for at least one of providing a liquid or gas to the interior chamber or exhausting a liquid or gas from the interior chamber.

11. The balloon catheter of claim 8, wherein the elongate member comprises a guidewire lumen.

12. The balloon catheter of claim 8, wherein the elongate member is constructed from a material that is substantially non-compressible longitudinally, such that translation of the elongate member at the port component causes a corresponding translation of the elongate member in the interior chamber of a substantially equivalent extent.

13. The balloon catheter of claim 12, wherein the elongate member comprises at least one of a braided material or a hypotube.

14. The balloon catheter of claim 1, further comprising a sheath configured to receive the catheter shaft and the inflatable balloon; wherein the inflatable balloon is configured to be advanced through the sheath to a treatment site outside the sheath and inflated for the treatment procedure, and deflated and withdrawn back into the sheath following the treatment procedure.

15. The balloon catheter of claim 14, wherein the spring member is configured to exert the distally-oriented longitudinal force in a manner that facilitates deflation and withdrawal of the inflatable balloon into the sheath.

16. A balloon catheter comprising:
a catheter shaft having a distal end to which is anchored a proximal end of an inflatable balloon;
a sheath that surrounds the catheter shaft, and that is configured to surround the inflatable balloon before and after a treatment procedure; wherein the inflatable balloon is configured to be moved to a treatment site outside of the sheath and inflated during the treatment procedure;
an elongate member that is separate from and disposed inside the catheter shaft, extends into an interior chamber of the inflatable balloon, is anchored to a distal end of the inflatable balloon, and is anchored to a proximal end of the catheter shaft; and
a spring member that exerts a distally-oriented longitudinal force on the elongate member, relative to the catheter shaft, wherein the distally-oriented longitudinal force causes the inflatable balloon to be biased in an extended position, away from the end of the catheter shaft, in a manner that facilitates deflation and withdrawal of the inflatable balloon into the sheath following the treatment procedure; wherein some slack in the form of an extra length of the elongate member is disposed between the proximal end of the catheter shaft and the spring member.

17. The balloon catheter of claim 16, wherein the elongate member comprises at least one of a guidewire lumen, a supply lumen for supplying a liquid or gas from an external source to the interior chamber, or an exhaust lumen for exhausting a liquid or gas from the interior chamber to a region exterior to the balloon catheter.

18. The balloon catheter of claim 16, wherein the spring member is disposed inside the catheter shaft and in close proximity to the distal end of the catheter shaft.

19. The balloon catheter of claim 16, wherein the spring member is disposed in a port component at the proximal end of the catheter shaft; and wherein the port component is configured to fluidly couple a device that is external to the balloon catheter to the interior chamber via one or more lumens disposed in the catheter shaft.

20. The balloon catheter of claim 16, wherein the inflatable balloon is configured to deliver cryotherapy to a treatment site internal to a patient's vasculature.

21. A method of providing therapy to a patient, the method comprising:
introducing a balloon catheter to a region internal to a patient and adjacent to a treatment site, wherein the balloon catheter comprises a) a catheter shaft having a proximal end and a distal end; b) an inflatable balloon having a proximal end that is anchored to the distal end of the catheter shaft; c) a sheath that surrounds the catheter shaft and initially surrounds the inflatable balloon; d) an elongate member that is separate from and disposed inside the catheter shaft, extends into an interior chamber of the inflatable balloon, is anchored to a distal end of the inflatable balloon, and is anchored to the proximal end of the catheter shaft; and e) a spring member that exerts a distally-oriented longitudinal force on the elongate member, relative to the catheter shaft, to bias the inflatable balloon in an extended position, away from the end of the catheter shaft;
advancing the balloon outside the sheath, inflating the balloon in a manner that causes the spring member to be compressed to a greater extent than an initial compressed state, thereby creating slack in the elongate member between the proximal end of the catheter shaft and the spring member, and delivering with the balloon therapy at the treatment site;
deflating the balloon; and
withdrawing the balloon into the sheath when the spring member has biased the deflated balloon in an extended position.

22. The method of claim 21, wherein delivering therapy comprises at least one of delivering cryotherapy, delivery radio frequency energy with a source disposed in the interior chamber, or placing a stent.

* * * * *